United States Patent [19]

Hagarty

[11] 3,956,498
[45] May 11, 1976

[54] INSECTICIDAL COMPOSITIONS CONTAINING 1,2,4-OXADIAZOLE AND THIADIAZOLE ESTERS

[75] Inventor: John D. Hagarty, Sturtevant, Wis.

[73] Assignee: S. C. Johnson & Son, Inc., Racine, Wis.

[22] Filed: Feb. 3, 1975

[21] Appl. No.: 546,638

Related U.S. Application Data

[62] Division of Ser. No. 331,164, Feb. 9, 1973, Pat. No. 3,879,407.

[52] U.S. Cl. ................................ 424/270; 424/272
[51] Int. Cl.² ...................... A01N 9/22; A01N 9/28
[58] Field of Search ............................ 424/270, 272

[56] References Cited

UNITED STATES PATENTS

| 3,270,028 | 8/1966 | Palazzo | 260/307 G |
|---|---|---|---|
| 3,432,519 | 3/1969 | Metivier et al. | 260/307 G |
| 3,792,079 | 2/1974 | D'Orazio | 260/468 H |
| 3,822,358 | 7/1974 | Okuno et al. | 424/285 |
| 3,879,407 | 4/1975 | Hagarty | 260/302 D |

*Primary Examiner*—Leonard Schenkman

[57] ABSTRACT

Novel 1,2,4-oxadiazole and thiadiazole esters and compositions containing same are described. The esters are useful as insecticides.

9 Claims, No Drawings

INSECTICIDAL COMPOSITIONS CONTAINING 1,2,4-OXADIAZOLE AND THIADIAZOLE ESTERS

This is a division, of application Ser. No. 331,164, filed Feb. 9, 1973, now U.S. Pat. No. 3,879,407.

The present invention relates to new and useful esters of 1,2,4-oxadiazoles or thiadiazoles having insecticidal activity.

Current trends in the chemical control of insects call for inherently safer materials with low mammalian toxicity. Accordingly, there is a great demand for broad spectrum insecticides which are suitable for the high volume usage entailed in household, garden and agricultural applications. Of the several insecticide classes which demonstrate low mammalian toxicity and good biodegradability, pyrethrum, a naturally occurring insecticide mixture, has found widest use. Pyrethrin, the most active component of pyrethrum, is a widely used insecticide which has a high order of insecticidal activity and a low mammalian toxicity. Due to the high cost of pyrethrin and its related compounds, however, synthetic products have been prepared which have a similar structure and exhibit significant insecticidal activity.

The novel esters of the present invention can be described as pyrethroid esters which contain a 1,2,4-oxadiazole or thiadiazole ring as the planar group of the alcohol portion of the molecule.

The 1,2,4-oxadiazole or thiadiazole esters which are the subject of this invention may be represented by the formulas

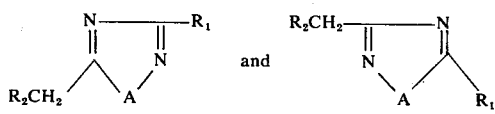

wherein A is oxygen or sulfur; $R_1$ is lower alkyl having 1–6 carbon atoms, benzyl, substituted benzyl (wherein the substituent is, for example, nitro, halo or lower alkyl having 1–6 carbon atoms), lower alkenyl having 1–6 carbon atoms, furylmethyl, cyclopentylmethyl, cyclopentenylmethyl, cyclohexenylmethyl and cyclohexylmethyl; and $R_2$ is the residue of a carboxylic acid wherein the carboxylic acid is selected from (+)-trans-chrysanthemumic acid, (±)- cis, trans-chrysanthemumic acid, dimethyl- and tetramethylcyclopropanecarboxylic acid, dihalocyclopropanecarboxylic acid, tetrahalocyclopropanecarboxylic acid and fenethric acid. It should be understood that the substituents on the cyclopropanecarboxylic acid are in the 2,2- or 2,2,3,3-position. It should also be understood that the scope of the invention is intended to include those isomeric compounds wherein the groups $R_1$ and —$CH_2R_2$ are in either the 3 or 5 positions of the ring. Either isomer can be prepared, as desired, from the appropriate starting materials, as will be apparent from the following disclosure and examples.

The novel 1,2,4-oxadiazole or thiadiazole esters of the present invention can be prepared by reacting the appropriate halomethyl-1,2,4-oxadiazole or thiadiazole with a carboxylic acid in the presence of a base. The halomethyl oxadiazoles and thiadiazoles may be depicted by the formulas

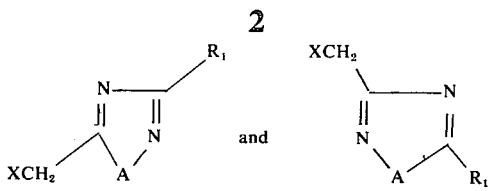

wherein X is a halogen such as chloro or bromo, and $R_1$ is as defined above.

The reaction is generally carried out at a temperature between room temperature and about 100°C. It is convenient, however, to carry out the reaction at the reflux temperature of the solvent. Solvents which are suitable for the reaction include acetone, ether, tetrahydrofuran, benzene and the like. The reaction is carried out from 1 to several hours depending upon the temperature employed. Generally, a reaction time of 6–12 hours is sufficient to complete the reaction. After the reaction is complete, the product is isolated by techniques known in the art. For example, the residue can be taken up in a suitable water immiscible solvent such as benzene, for example, and the solution washed with water, dilute acid, such as dilute hydrochloric acid and a basic solution such as a sodium bicarbonate solution. The 1,2,4-oxadiazole or thiadiazole ester is obtained on removal of the solvent and can be further purified by techniques known in the art.

The carboxylic acids, include acids such as (+) trans-chrysanthemumic acid, (±)-cis, trans-chrysanthemumic acid, 2,2-dimethylcyclopropanecarboxylic acid, 2,2,3,3-tetramethylcyclopropanecarboxylic acid, 2,2-dihalocyclopropanecarboxylic acid, 2,2,3,3-tetrahalocyclopropanecarboxylic acid wherein the halogen is chloro or bromo, and fenethric acid.

As the basic reactant, generally an organic basic amine such as triethylamine is employed. Other amines which are suitable for the reaction include pyridine and tri-n-propylamine. The relative amounts of the reactants employed are not critical, although it is desirable that excesses of either reactant be avoided to prevent undue amounts of side reactions. It is preferred that the two reactants be present in the reaction mixture in about stoichiometric proportions, i.e., about 1 mole of the halomethyl compound per mole of the carboxylic acid.

The halomethyl-1,2,4-oxadiazoles and thiadiazoles which are the starting materials for the esters are themselves novel compounds except for those compounds where A is oxygen and $R_1$ is methyl or benzyl.

Those compounds wherein the halomethyl group is in the 5-position can be prepared by reacting a substituted acetonitrile with hydroxylamine hydrochloride in aqueous alcohol in the presence of a base such as sodium carbonate, for example. The reaction is generally carried out at about 50°C. and the acetamide oxime intermediate is obtained upon removal of the solvent. The oxime intermediate is then reacted with a haloacetic anhydride in a suitable solvent such as toluene, for example. The product is generally obtained by distillation after removal of the solvent.

Those compounds wherein the halomethyl group is in the 3-position can be prepared by reacting a haloacetonitrile with hydroxylamine in the presence of a base such as sodium carbonate. The haloacetamide oxime which forms is then reacted with the appropriate substituted iminoacetate hydrochloride to obtain the corresponding 3-halomethyl compound.

The novel insecticidally active compounds provided by the present invention may be employed in combating a variety of crop pests and household pests. They are particularly useful in the control of houseflies and roaches.

In applying the products of this invention as insecticides, conventional techniques may be used. Good results are obtained when the compounds are applied as aerosol sprays, for example, or are formulated into any of the diluted and extended types of formulations commonly used in insecticidal practice, including dusts, wettable powders, emulsifiable concentrates, solutions, granulars, baits, and the like, for application to foliage, within closed areas, to surfaces, and wherever insect control is desired.

The compositions may be made into liquid concentrates by solution or emulsification in suitable liquids, and into solid concentrates by admixing with talc, clays, and other known solid carriers used in the insecticide art. These concentrates are compositions which normally contain about 10–50% of the toxicant with the remainder being inert materials such as dispersing agents, emulsifying agents and wetting agents. Minor amounts of other substances may be added to the compositions in order to obtain particular functional or esthetic effects. Substances such as perfumes, corrosion inhibitors, buffering agents, fillers, flame retardants, antioxidants, ultraviolet radiation absorbers, disinfectants and the like, are examples of such additives. The concentrates are diluted for practical application, with water or other liquids for liquid sprays or with additional solid carrier for application as a dust or granular formulation. Baits are usually prepared by mixing such concentrates with a suitable food, such as a mixture of cornmeal and sugar. The concentration of the toxicant in the diluted formulations, as generally applied for insect control, is normally in the range of about 2% to about 0.001%.

Because of the extremely low mammalian toxicity of the compositions containing the insecticidally active esters, they are preferred compositions for use in the control of pests in an environment inhabited by man and animals, including the control of flies, mosquitoes, ants, roaches, and the like.

The insecticidally active esters may be used alone or in combination with a synergist to enhance the insecticidal response. Any of the commonly used synergists such as piperonyl butoxide, dipropargyl phenyl phosphonate, sesamex and tropital, for example, may be employed. The preferred synergists are piperonyl butoxide and dipropargyl phenyl phosphonate.

The relative amounts of synergist and toxicant employed are not critical in that a relatively minor amount of synergist is effective in imparting a beneficial effect to the combination. The synergistic insecticidal compositions of this invention generally contain a ratio of ester to synergist from about 1:1 to about 1:10. The preferred ratio is from about 1:3 to 1:5. Even larger proportions of synergist may be employed without detriment, whether or not the optimum synergistic proportions have been achieved. It is clear that effective amounts of synergist should be employed in the composition and that the components should be present in synergistic proportions.

Although this invention has been described in detail with particular reference to preferred embodiments thereof, it will be understood that variations and modifications can be effected within the spirit and scope of this invention as described hereinabove and as defined in the appended claims.

EXAMPLE 1

A solution of 3-benzyl-5-chloromethyl-1,2,4-oxadiazole 20.8 g. (0.1 mole), (+) trans-chrysanthemumic acid, 16.8 g. (0.1 mole) and 10 g. (0.1 mole) of triethylamine is prepared in 120 ml. of dry acetone. The resultant mixture is refluxed for 6–12 hours after which the solvent is removed in vacuo and the residue taken up in 150 ml. of benzene. The benzene solution is washed with 100 ml. of water, 100 ml. of dilute hydrochloric acid and 100 ml. of sodium bicarbonate solution and then dried over magnesium sulfate. Upon removal of the solvent (+)- trans-chrysanthemumoxymethyl 3-benzyl-1,2,4-oxadiazole is obtained as a viscous oil having an index of refraction of $N^{20}$ 1.5250.

The following compounds were prepared in accordance with the procedure outlined in Example 1.

TABLE I

| Example No. | $R_2$ | $R_1$ | $n^{20}$ |
| --- | --- | --- | --- |
| 2 | 2,2,3,3-tetramethylcyclopropanecarboxylic acid | 3-benzyl | 1.5310 |
| 3 | fenethric acid | 3-benzyl | 1.5413 |
| 4 | ± cis, trans-chrysanthemumic acid | 3-benzyl | 1.5154 |
| 5 | + trans-chrysanthemumic acid | 5-benzyl | 1.5288 |
| 6 | 2,2,3,3-tetramethylcyclopropanecarboxylic acid | 5-benzyl | 1.5209 |
| 7 | + trans-chrysanthemumic acid | 3-allyl | 1.4886 |
| 8 | 2,2,3,3-tetramethylcyclopropanecarboxylic acid | 3-allyl | 1.4786 |
| 9 | + trans-chrysanthemumic acid | 3-furylmethyl | 1.4921 |
| 10 | + trans-chrysanthemumic acid | 3-(1,2-cyclopentenylmethyl) | 1.4996 |
| 11 | + trans-chrysanthemumic acid | 3-(1,2,-cyclohexenylmethyl) | 1.5031 |
| 12 | + trans-chrysanthemumic acid | 3-isopropyl | 1.4769 |
| 13 | + trans-chrysanthemumic acid | 3-methyl | 1.4818 |
| 14 | + trans-chrysanthemumic acid | 3-(p-nitrobenzyl) | 1.5414 |

The 3,5-disubstituted-1,2,4-oxadiazoles which are the starting materials for the present invention are prepared as follows:

EXAMPLE 15

3-benzyl-5-chloromethyl-1,2,4-oxadiazole

A. A solution of 117.2 g. (1 mole) of phenylacetonitrile and 69.5 g. (1 mole) of hydroxylamine hydrochloride in 500 ml. of aqueous ethanol is treated with 106 g. of sodium carbonate. The mixture is then heated to 50°C. and held at this temperature for two days. After cooling, the sodium chloride which forms is filtered off and the solvent is removed in vacuo. Upon recrystallization of the crystalline residue from aqueous methanol, colorless needles of phenylacetamide oxime having a m.p. of 55°–60°C. are obtained.

B. A solution of 40 g. (0.27 mole) of crude phenylacetamide oxime in 200 ml. of dry toluene is treated with 45.9 g. (0.27 mole) of chloroacetic anhydride in 100 ml. of toluene. The resultant mixture is then refluxed and the water formed is removed by means of a Dean Stark trap. The mixture is refluxed for 3-4 hours after which it is cooled and extracted once with 150 ml. of water and four times with 100 ml. of a saturated sodium bicarbonate solution. The toluene solution is then dried over magnesium sulfate and the solvent is removed in vacuo. Upon distillation of the residue, 3-benzyl-5-chloromethyl-1,2,4-oxadiazole, 19.8 g. having a b.p. of 100–108 (0.04 mm) is obtained.

EXAMPLE 16

3-chloromethyl-5-benzyl-1,2,4-oxadiazole

A. A solution of chloroacetonitrile, 75 g. (1.0 mole)

The following examples illustrate the insecticidal activity of the compounds of this invention. They also illustrate the unexpectedly high order of synergism obtained when these compounds are combined with dipropargyl phenylphosphonate. In each case where a synergist was employed, it was used at the ratio of 4 parts by weight of synergist per part by weight of toxicant. The numerical results reported in the table are the ratio of the activity of the test toxicant to the activity of a combination of 4 parts of piperonylbutoxide with one part of pyrethrin, a commercially employed, potent toxicant formulation.

| | | OXADIAZOLE ESTERS - TOXICANT RATIO | | | | | | Peet-Grady Knockdown | | | | | |
|---|---|---|---|---|---|---|---|---|---|---|---|---|---|
| | Synergist | Topical Application | | | | | | 3" | | 5" | | 10" | |
| | | Housefly | | | German Roach | | | | | | | | |
| Example Number | Oxadiazole Ester[1] | None | PB[2] | DPPP[3] | None | PB | DPPP | None | PB | None | PB | None | PB |
| 24 | 3-benzyl | .12±.01 | .91±.09 | 1.44±.15 | .08±.01 | .08±.01 | .94±.14 | .27 | .38 | .55 | .79 | .71 | .95 |
| 25 | 3-benzyl | .06±.006 | .40 ±.04 | .73±.08 | NIL | NIL | .35±.05 | .16 | .24 | .24 | .30 | .19 | .29 |
| 26 | 3-allyl | .025±.003 | .26±.02 | .39±.04 | NIL | NIL | .08±.01 | .13 | .16 | .16 | .16 | .30 | .30 |
| 27 | 3-furylmethyl | .041±.005 | .34±.04 | .68±.06 | .04±.01 | .05±.01 | .18±.03 | .19 | .22 | .34 | .47 | .58 | .65 |
| 28 | 5-benzyl | .044±.006 | .45±.05 | .66±.07 | NIL | NIL | .30±.05 | .13 | .17 | .12 | .18 | .46 | .42 |

[1]In Examples 25-27, the compound tested corresponded to the generic formula given above wherein R$_2$ is (±) - cis, trans chrysanthemumic acid. In Examples 24 and 28, R$_2$ is (+) - trans chrysanthemumic acid.
[2]PB = piperonyl butoxide
[3]DPPP = dipropargyl phenylphosphonate.

and hydroxylamine hydrochloride, 69.5 g. (0.1 mole), in 250 ml. of water is prepared. The solution is then carefully treated with 53 g. of sodium carbonate while keeping the temperature below 30°C. The mixture is held at 30°C. for 15 minutes after which it is extracted with ether several times. Sodium chloride is added to facilitate extraction. The ether extracts are combined and dried over magnesium sulfate. The solvent is removed in vacuo and crude crystalline oxime is obtained. Upon recrystallization from benzene, 56 g. of chloroacetamide oxime is obtained having a n/m.p. of 86°-88°C.

B. A mixture of chloroacetamide oxime, 11.0 g. (0.10 mole), and ethyl phenyliminoacetate hydrochloride, 22 g. (0.11 mole), in 80 ml. of absolute ethanol is refluxed for one hour. After cooling, the ammonium chloride which precipitates is filtered off and the alcohol is removed in vacuo. Upon steam distillation of the residue, 7.0 gm. of 3-chloromethyl-5-benzyl-1,2,4-oxadiazole is obtained, $n^{20}$ 1.5386.

The following compounds were prepared in accordance with the procedure outlined in Example 16 above.

| Example No. | X | R$_1$ | b.p. | $n^{20}$ |
|---|---|---|---|---|
| 17 | Cl | 3-allyl | — | 1.4826 |
| 18 | Cl | 3-furylmethyl | 96–101°C (0.12 mm) | 1.5036 |
| 19 | Cl | 3-cyclopentenyl-methyl | 88–94°C (0.12 mm) | 1.5034 |
| 20 | Cl | 3-cyclohexenyl-methyl | 96–99°C (0.07 mm) | 1.5094 |
| 21 | Cl | 3-isopropyl | 76–79°C (10 mm) | 1.4576 |
| 22 | Cl | 3-ethyl | 88–89°C (35 mm) | 1.4619 |
| 23 | Cl | 3-p-nitrobenzyl | m.p. 50–52°C | |

What is claimed:

1. An insecticidal composition consisting essentially of a major proportion of a non-toxic inert carrier and a minor, but effective proportion as an essential active component thereof of a compound of the formula

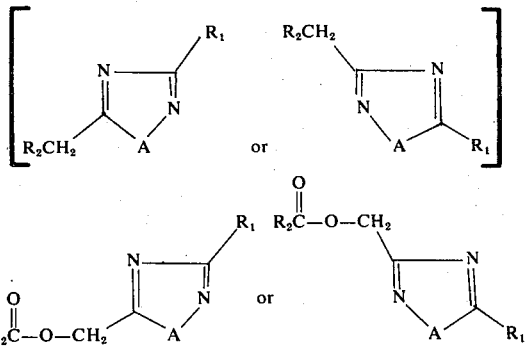

wherein A is oxygen or sulfur, R$_1$ is selected from the group consisting of benzyl, substituted benzyl wherein the substituent is nitro, halo or lower alkyl having 1–6 carbon atoms, lower alkyl having 1–6 carbon atoms, lower alkenyl having 1–6 carbon atoms, furylmethyl, cyclopentylmethyl, cyclopentenylmethyl, cyclohexenylmethyl, and cyclohexylmethyl, and R$_2$ is the residue of a carboxylic acid selected from the group consisting of (+)-trans-chrysanthemumic acid, (±)-cis, trans-chrysanthemumic acid, dimethylcyclopropanecarboxylic acid, tetramethylcyclopropanecarboxylic acid, dihalocyclopropanecarboxylic acid, and tetrahalocyclopropanecarboxylic acid.

2. The composition of claim 1 wherein A is oxygen, R$_1$ is benzyl and R$_2$ is the residue of a carboxylic acid selected from the group consisting of (+)-trans-chrysanthemumic acid, (±)-cis, trans-chrysanthemumic acid, dimethylcyclopropanecarboxylic acid, tetramethylcyclopropanecarboxylic acid, dihalocyclopropanecarboxylic acid, and tetrahalocyclopropanecarboxylic acid.

3. A synergistic insecticidal composition comprising an insecticidally effective amount of a compound of the formula

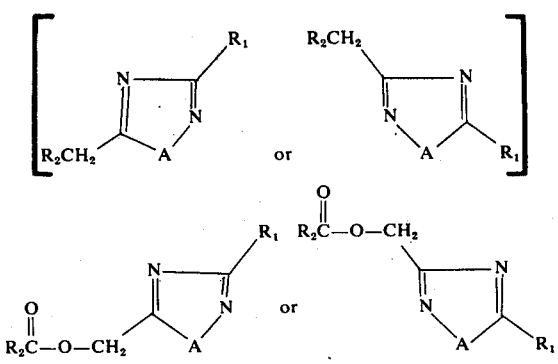

wherein A is oxygen or sulfur, R₁ is selected from the group consisting of benzyl, substituted benzyl wherein the substituent is nitro, halo or lower alkyl having 1–6 carbon atoms, lower alkyl having 1–6 carbon atoms, lower alkenyl having 1–6 carbon atoms, furylmethyl, cyclopentylmethyl, cyclopentenylmethyl, cyclohexenylmethyl, and cyclohexylmethyl and R₂ is the residue of a carboxylic acid selected from the group consisting of (+)-trans-chrysanthemumic acid, (±)-cis, trans-chrysanthemumic acid, dimethylcyclopropanecarboxylic acid, tetramethylcyclopropanecarboxylic acid, dihalocyclopropanecarboxylic acid, and tetrahalocyclopropanecarboxylic acid and an effective amount of a synergist to synergize said compound.

4. The synergistic insecticidal composition of claim 1 wherein A is oxygen, R₁ is benzyl and R₂ is the residue of a carboxylic acid selected from the group consisting of (+)-trans-chrysanthemumic acid, (±)-cis, trans-chrysanthemumic acid, dimethylcyclopropanecarboxylic acid, tetramethylcyclopropanecarboxylic acid, dihalocyclopropanecarboxylic acid, and tetrahalocyclopropanecarboxylic acid.

5. The composition of claim 4 wherein the synergist is selected from the group consisting of piperonyl butoxide, dipropargyl phenyl phosphonate, sesamex and piperonal bis [2-(2'-n-butoxyethoxy) ethyl] acetal.

6. The composition of claim 5 wherein the synergist is piperonyl butoxide.

7. The composition of claim 5 wherein the synergist is dipropargyl phenylphosphonate.

8. The composition of claim 5 wherein said compound and synergist are present in a ratio of 1:1 to 1:10.

9. The composition of claim 8 wherein said ratio is 1:3 to 1:5.

* * * * *

UNITED STATES PATENT OFFICE
CERTIFICATE OF CORRECTION

Patent No. 3,956,498  Dated May 11, 1976

Inventor(s) John D. Hagarty

It is certified that error appears in the above-identified patent and that said Letters Patent are hereby corrected as shown below:

Column 2, line 28, insert a hyphen after "(+)".

Column 5, line 38, "n/m.p." should be --m.p.---.
Claim 1, the formula within brackets should be deleted.
Claim 3, the formula within brackets should be deleted.
Claim 4 should be dependent upon claim 3, not claim 1.

Signed and Sealed this

Twelfth Day of October 1976

[SEAL]

Attest:

RUTH C. MASON  
Attesting Officer

C. MARSHALL DANN  
Commissioner of Patents and Trademarks